(12) United States Patent
Hanson et al.

(10) Patent No.: US 10,907,217 B1
(45) Date of Patent: Feb. 2, 2021

(54) **HIGH RESOLUTION MELT-CURVE ANALYSIS TO IDENTIFY THE SEQUENCE TYPE OF *E. COLI***

(71) Applicant: Creighton University, Omaha, NE (US)

(72) Inventors: Nancy D. Hanson, Omaha, NE (US); Lucas Harrison, Omaha, NE (US)

(73) Assignee: Creighton University, Omaha, NE (US)

( * ) Notice: Subject to any disclaimer, the term of this patent is extended or adjusted under 35 U.S.C. 154(b) by 201 days.

(21) Appl. No.: 15/254,626

(22) Filed: Sep. 1, 2016

Related U.S. Application Data

(60) Provisional application No. 62/212,918, filed on Sep. 1, 2015.

(51) Int. Cl.
*C12Q 1/689* (2018.01)

(52) U.S. Cl.
CPC .................................. *C12Q 1/689* (2013.01)

(58) Field of Classification Search
None
See application file for complete search history.

(56) References Cited

U.S. PATENT DOCUMENTS

| | | | | |
|---|---|---|---|---|
| 2007/0292859 A1* | 12/2007 | Kozian | ............... | C12Q 1/6883 435/6.11 |
| 2010/0167288 A1* | 7/2010 | Gale | ............... | B01L 3/502707 435/6.19 |
| 2011/0014606 A1* | 1/2011 | Steinmetzer | ......... | B01J 19/0046 435/6.11 |

OTHER PUBLICATIONS

Dhanji et al. Real-time PCR for detection of the O25b-ST131 clone of *Escherichia coli* and its CTX-M-15-like extended-spectrum β-lactamases. International Journal of Antimicrobial Agents 36:355-358. (Year: 2010).*
Woksepp et al. High-resolution melting-curve analysis of ligation-mediated real-time PCR for rapid evaluation of an epidemiological outbreak of extended-spectrum-beta-lactamase-producing *Escherichia coli*. Journal of Clinical Microbiology 49(12):4032-4039. (Year: 2011).*
Lafolie et al. Prevalence of *Escherichia coli* sequence type 131 and its H30 subclone among *E. coli* isolates in a French hospital. International Journal of Antimicrobial Agents 44:466-468. (Year: 2014).*
Veenemans et al. Next-generation sequencing for typing and detection of resistance genes: performance of a new commercial method during an outbreak of extended-spectrum-beta-lactamase-producing *Escherichia coli*. Journal of Clinical Microbiology 52(7): 2454-2460. (Year: 2014).*
Brady et al. Probe-based real-time PCR method for multilocus melt typing of *Xylella fastidiosa* strains. Journal of Microbiological Methods 89:12-17. (Year: 2012).*
Johnson et al. Molecular Epidemiological Analysis of *Escherichia coli* Sequence Type ST131 (O25:H4) and blaCTX-M-15 among Extended-Spectrum-β-Lactamase-Producing *E. coli* from the United States, 2000 to 2009. Antimicrobial Agents and Chemotherapy 56(5):2364-2370. (Year: 2012).*
Richardson et al. Preliminary validation of a novel high-resolution melt-based typing method based on the multilocus sequence typing scheme of *Streptococcus pyogenes*. Clinical Microbiology and Infection 17:1426-1434. (Year: 2011).*
Nicolas-Chanoine, M.H. et al., "*Escherichia coli* ST131, an Intriguing Clonal Group", J. Clin. Microbiol Rev 2014:27:3 543-574.
Peirano, G. et al., "The characteristics of *Escherichia coli* ST131 that produce extended-spectrum β-lactamases: global distribution of the H30-Rx sublineage", Antimicrob Agents Ch 2014;doi: 10.1128/AAC.02428-14.
Colpan, A. et al., "*Escherichia coli* Sequence Type 131 (ST131) Subclone H30 as an Emergent Multidrug-Resistant Pathogen Among US Veterans", Clin. Infect Dis. 2013;57:9 1256-65.
Kuo, S. et al., "Colistin resistance gene mcr-1 in *Escherichia coli* isolates from humans and retail meats, Taiwan", J. Antimicrob. Chemother. 2016;doi: 10.1093/jac/dkw122.
Banerjee, R. et al., "*Escherichia coli* sequence type 131 is a dominant, antimicrobial-resistant clonal group associated with health-care and elderly hosts", Infect Cont. Hosp. Ep. 2013;34:4 361-369.
Mathers, A. J., "*Escherichia coli* ST131: The Quintessential Example of an International Multiresistant High-Risk Clone", Adv. Appl. Microbiol. 2014;90 109-154.
Joensen, K. G. et al., "Real-Time Whole-Genome Sequencing for Routine Typing, Surveillance, and Outbreak Detection of Verotoxigenic *Escherichia coli*", Clin. Infect Dis. 2014;52(5):1501-1510.
Cai, J. C. et al., "Emergence of *Escherichia coli* Sequence Type 131 Isolates Producing KPC-2 Carbapenemase in China", Antimicrob. Agents Ch 2014;58:2 1146-1152.
Bae, I. K., et al., "Comparison of pulsed-field gel electrophoresis & repetitive sequence-based PCR methods for molecular epidemiological studies of *Escherichia coli* clinical isolates", Indian J. Med. Res. 2014;140:5 679-685.
Mazi, W. et al., "Rapid genotyping of Shigella sonnei using mutiplex high resolution melting", J. Clin. Microbiol. 2015; doi:10.1128/JCM.00874-15.
Dwight, Z. et al., "uMELT: prediction of high-resolution melting curves and dynamic melting profiles of PCR products in a rich web application", Bioinformatics 2011;27:7 1019-1020.

(Continued)

*Primary Examiner* — Samuel C Woolwine
(74) *Attorney, Agent, or Firm* — Mallory M. Henninger; Advent, LLP

(57) ABSTRACT

Methods for differentiating *E. coli* sequence type 131 are described. In one implementation, a method that employs example techniques in accordance with the present disclosure for determining *E. coli* sequence type 131 includes amplifying a gene target in the presence of a fluorescent reporter dye; exposing the gene target and the fluorescent reporter dye to an increasing temperature gradient to denature and reduce the helicity of a double-stranded oligo of the gene target; recording fluctuations in fluorescence using a High Resolution Melting analysis (HRM)-capable thermocycler; and producing a melt curve unique to the gene target.

8 Claims, 6 Drawing Sheets

(56) References Cited

OTHER PUBLICATIONS

Hjelmso, M. H. et al., "High-Resolution Melt Analysis for Rapid Comparison of Bacterial Community Compositions", Appl. Environ. Microbiol. 2014;80:12 3568-3575.
Wittwer, C. T. et al., "High-Resolution Genotyping by Amplicon Melting Analysis Using LCGreen", Clin. Chem. 2003;49:6 853-860.
Woksepp, H. et al., "Evaluation of High-Resolution Melting Curve Analysis of Ligation-Mediated Real-Time PCR, a Rapid Method for Epidemiological Typing of ESKAPE (Enterococcus Faecium, *Staphylococcus aureus*, Klebsiella pneumoniae, Acinetobacter baumannii, Pseudomonas aeruginosa, and *Enterobacter* Species) Pathogens", J. Clin. Microbiol. 2014;52:12 4339-4342.
Vossen, R. et al., "High-Resolution Melting Analysis (HRMA)—More Than Just Sequence Variant Screening", Hum. Mutat. 2009;30:6 860-866.
Kim, Y.A. et al., "Features of Infections Due to Klebsiella pneumoniae Carbapenemase-Producing *Escherichia coli*: Emergence of Sequence Type 131", Clin. Infect. Dis. 2012;55:224-231.
Lau, S. H. et al., "Major Uropathogenic *Escherichia coli* Strain Isolated in the Northwest of England Identified by Multilocus Sequence Typing", J. Clin. Microbiol. 2008;46:3 1076-1080.
Johnson, J. R. et al., "Rapid and Specific Detection, Molecular Epidemiology, and Experimental Virulence of the O16 Subgroup within *Escherichia coli* Sequence Type 131", J. Clin. Microbiol. 2014;52:5 1358-1365.
Core, R. et al., "A language and environment for statistical computing", R. Foundation for Statistical Computing, Vienna, Austria 2015.
Adler, D. et al., 3D visualization Using OpenGL. R package version 0.95.1337.2015.
Fraley, C. et al., "mclust Version 4 for R: Normal Mixture Modeling for Model-Based Clustering, Classification, and Density Estimation", Technical Report No. 597, Department of Statistics, University of Washington 2012.
Fraley, C. et al., "Model-based Clustering, Discriminant Analysis and Density Estimation", J. Amer. Statist. Assoc. 2002;97:611-63.
Clermont, O. et al., "Development of an allele-specific PCR for *Escherichia coli* B2 sub-typing, a rapid and easy to perform substitute of multilocus sequence typing", J. Microbiol. Meth. 2014;101 24-27.
Doumith, M. et al., "Rapid Identification of Major *Escherichia coli* Sequence types Causing Urinary Tract and Bloodstream Infections", J. Clin. Microbiol. 2015;53:1 160-166.
Momeni, S.S. et al., "Comparative genotyping of *Streptococcus mutans* by repetitive extragenic palindromic polymerase chain reaction and multilocus sequence typing", Mol. Oral Microbiol. 2012;28:1 18-27.
Banjeree, R. et al., "A New Clone Sweeps Clean: the Enigmatic Emergence of *Escherichia coli* Sequence Type 131", Antimicrob Agents Ch. 2014;58:9 4997-5004.
Athamanolap, P. et al., "Trainable High Resolution Melt Curve Machine Learning Classifier for Large-Scale Reliable Genotyping of Sequence Variants", PloS One 2014;9-10e109094.
Ben-Hur, A. et al., "Detecting Stable Clusters Using Principal Component Analysis" In M. J. Brownstein and A. Kohodursky (eds.), Functional Genomics: Methods and Protocols, Humana Press, New York City, NY 2003; 159-182.

\* cited by examiner

US 10,907,217 B1

HIGH RESOLUTION MELT-CURVE ANALYSIS TO IDENTIFY THE SEQUENCE TYPE OF E. COLI

CROSS-REFERENCE TO RELATED APPLICATIONS

The present application claims the benefit under 35 U.S.C. § 119(e) of U.S. Provisional Application Ser. No. 62/212,918, filed Sep. 1, 2015, and titled "HIGH RESOLUTION MELT-CURVE ANALYSIS TO IDENTIFY THE SEQUENCE TYPE OF E. COLI" U.S. Provisional Application Ser. No. 62/212,918 is herein incorporated by reference in its entirety.

BACKGROUND

E. coli belonging to the sequence type 131 clonal complex (ST131) have been associated with the global distribution of ESBL resistance genes, particularly the CTX-Ms. Multi Locus Sequence Typing (MLST) of 7 genes can be used to identify the presence of this strain of E. coli in a health care setting. Whole genome sequencing and MLST analysis can be used to identify the sequence type.

SUMMARY

The present disclosure relates to methods for differentiating the E. coli sequence type 131 from other sequence types without the need to sequence PCR amplicons.

In one implementation, a method for determining E. coli sequence type 131 includes amplifying a gene target in the presence of a fluorescent reporter dye; exposing the gene target and the fluorescent reporter dye to an increasing temperature gradient to denature and reduce the helicity of a double-stranded oligo of the gene target; recording fluctuations in fluorescence using a High Resolution Melting analysis (HRM)-capable thermocycler; and producing a melt curve unique to the gene target.

In one implementation, a method for differentiating E. coli sequence type 131 includes recording fluctuations in fluorescence of a gene target and a fluorescent reporter dye under an increasing temperature gradient by using a High Resolution Melting analysis (HRM)-capable thermocycler; and producing a melt curve unique to the gene target.

In one implementation, a method for differentiating E. coli sequence type 131 using High Resolution Melt-curve analysis includes extracting a sample of DNA; performing a singleplex polymerase chain reaction using the sample of DNA, a buffer, and at least one multilocus sequence typing (MLST) primer resulting in at least one amplicon; performing a multiplex polymerase chain reaction using the sample of DNA and the at least one amplicon; determining a melt temperature peak using (HRM) analysis of the sample of DNA; and providing a melt profile corresponding to the sample of DNA.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

Figure 2A:
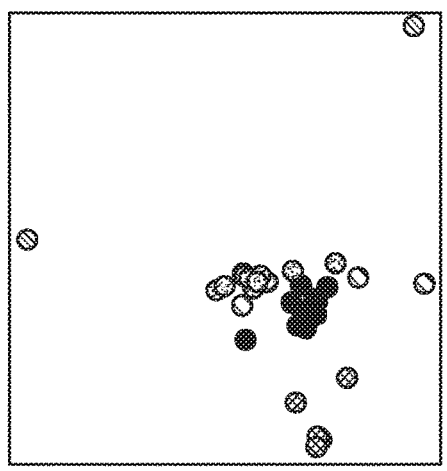
Figure 2A:
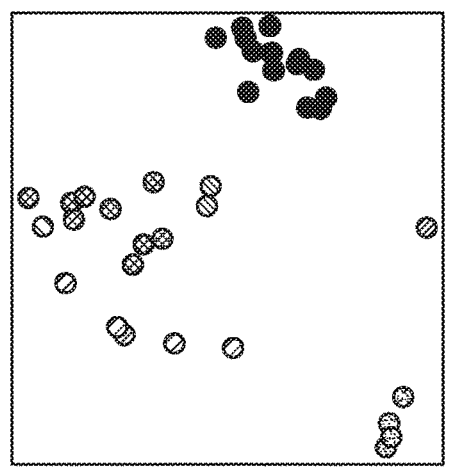
Figure 2A:
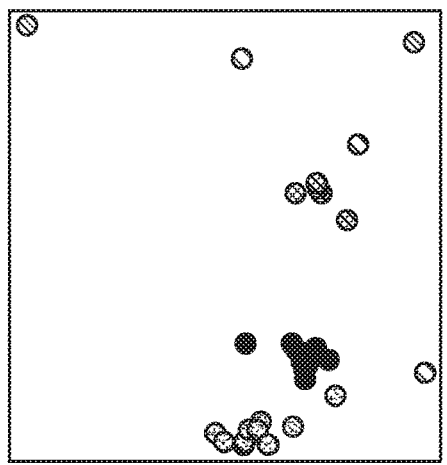
Figure 2A:
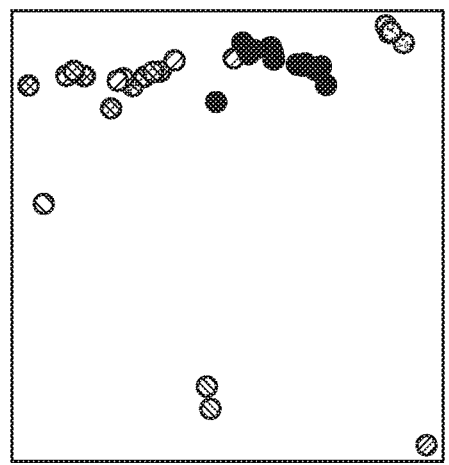
Figure 2A:
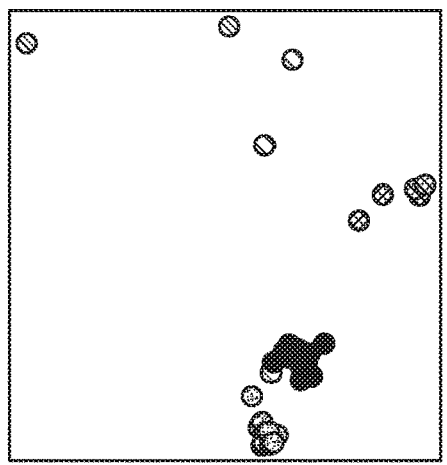
Figure 2A:
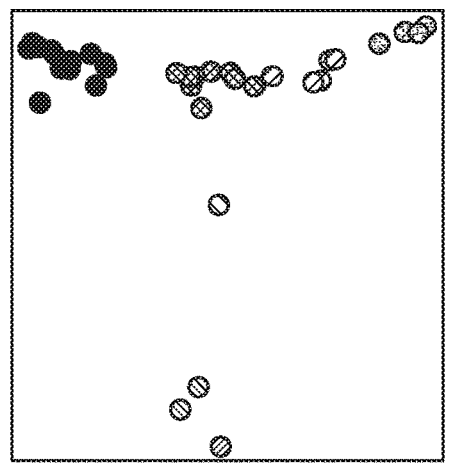

FIG. 2A is a graphical illustration depicting PCA visualization of E. coli MLST amplicon residual melt profile data from an ABI 7500 Fast PCR Thermocycler using open source R programming language. Isolates were grouped into clusters based on similarity of PCA profiles. Solid black clusters are identified as ST131s while the other coded clusters indicate groups of unknown sequence types.

Figure 2B:
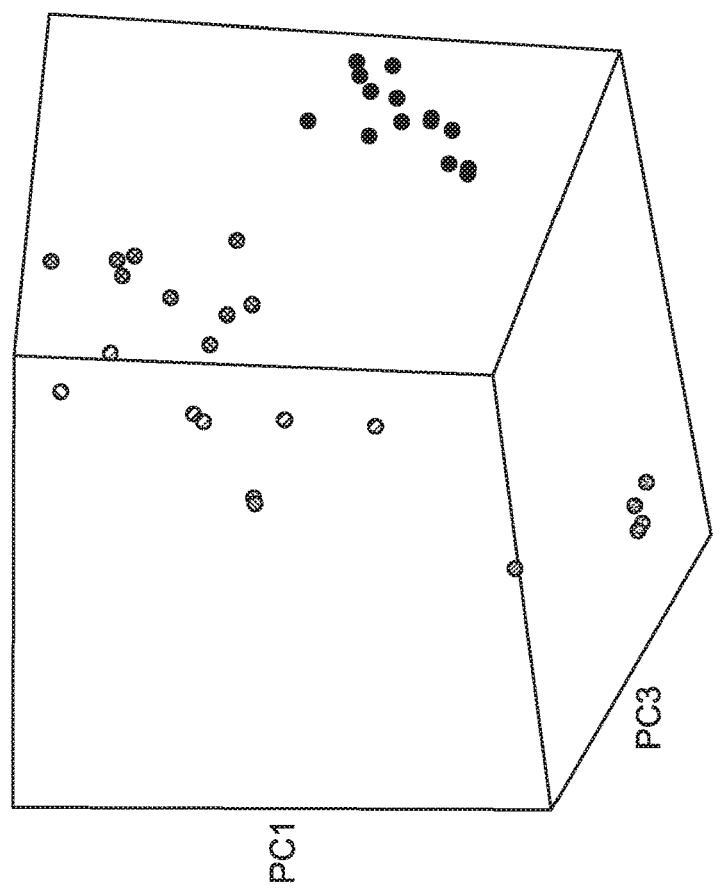
Figure 2B:
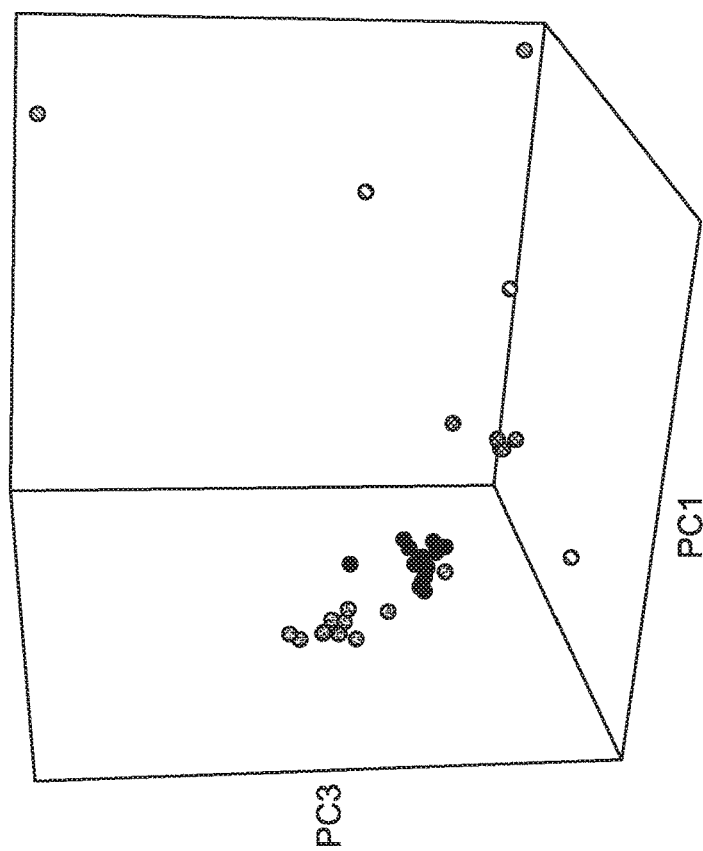

FIG. 2B is a graphical illustration depicting the three 2D PCA plots from FIG. 2A for each master mix combined into an interactive 3D model to facilitate analysis. The solid black clusters represent ST131 E. coli.

Figure 3:
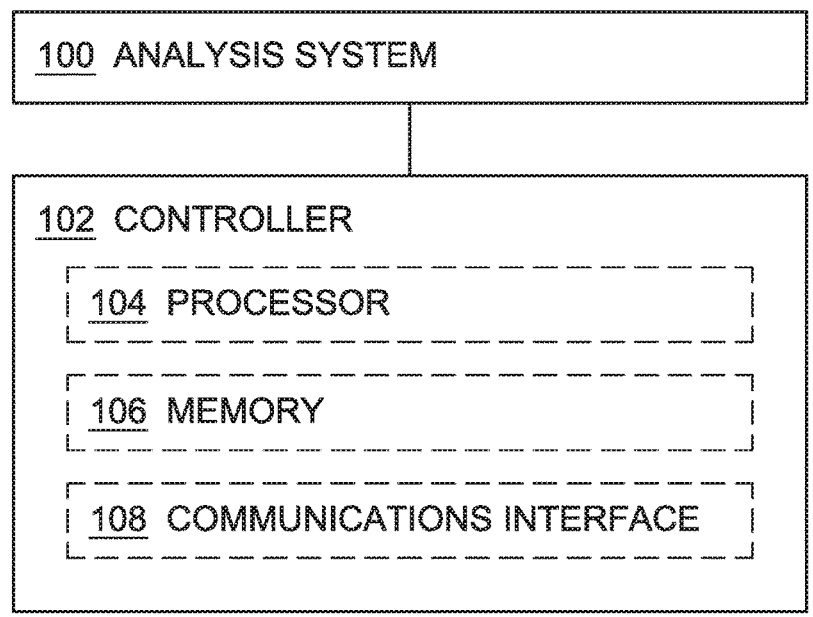

FIG. 3 is an environmental view illustrating an analysis device for determining E. coli sequence type 131, where the analysis device is coupled to a controller, in accordance with an example implementation of the present disclosure.

Figure 4:
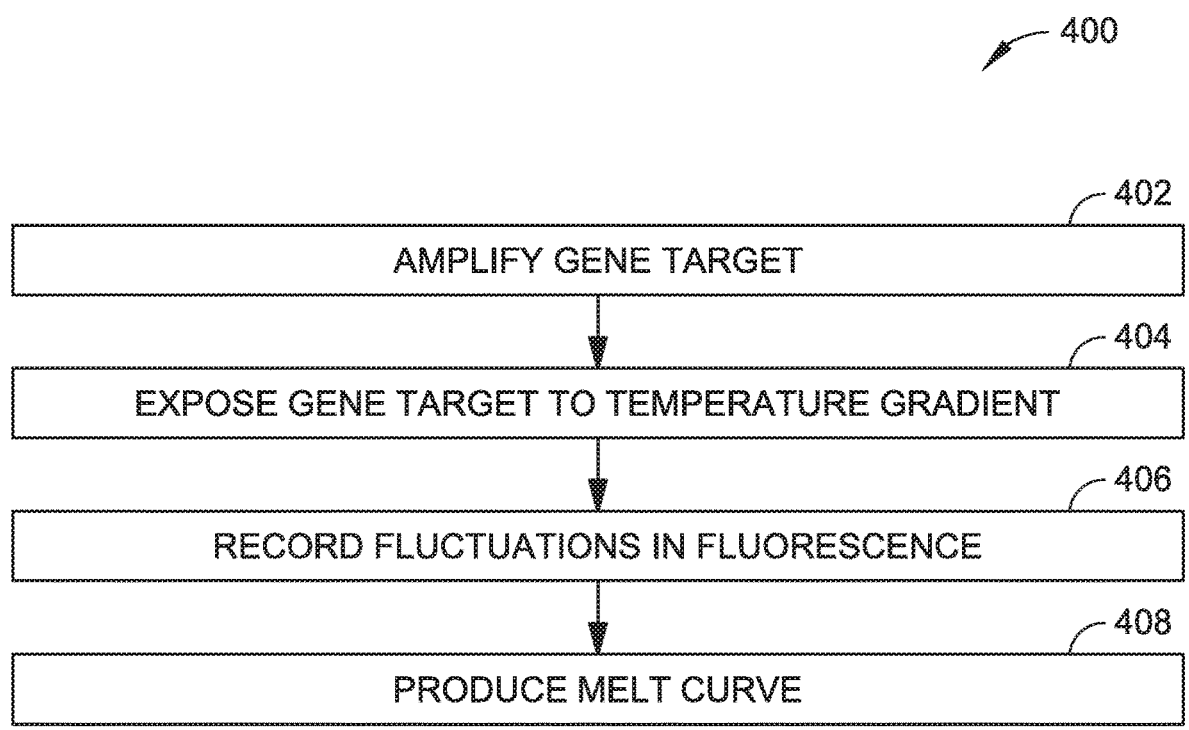

FIG. 4 is a flow diagram illustrating a method in an example implementation for determination of E. coli sequence type 131 using an analysis system, such as the analysis system shown in FIG. 3.

Figure 5:
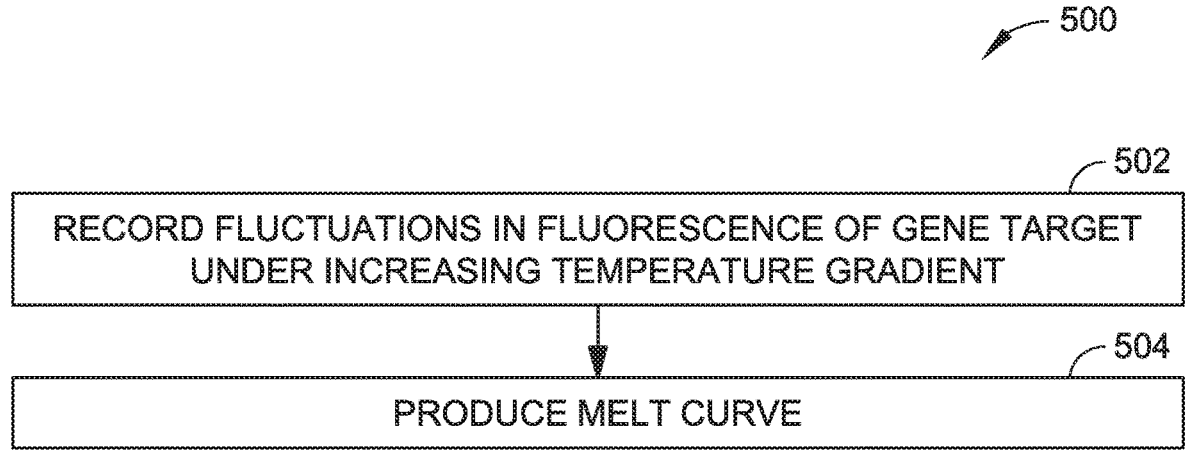

FIG. 5 is a flow diagram illustrating a method in an example implementation for determination of E. coli sequence type 131 using an analysis system, such as the analysis system shown in FIG. 3.

Figure 6:
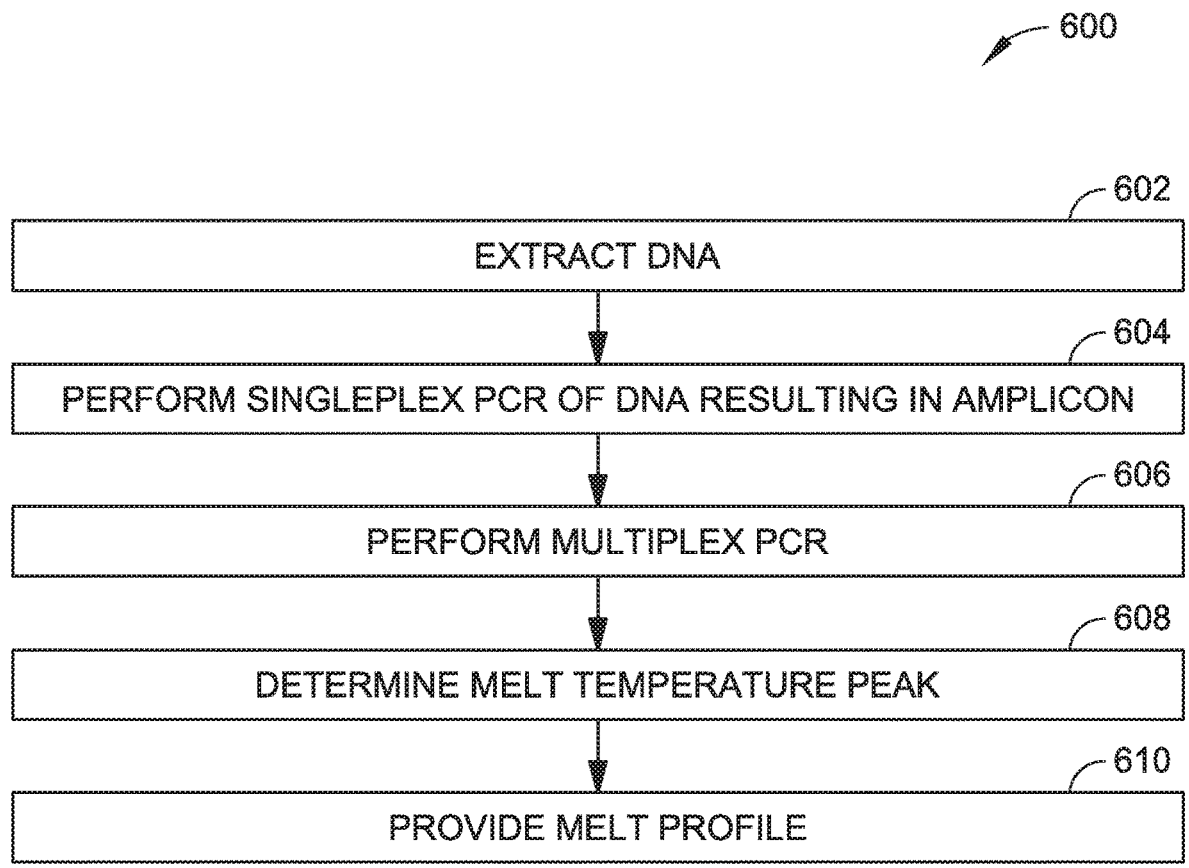

FIG. 6 is a flow diagram illustrating a method in an example implementation for determination of E. coli sequence type 131 using an analysis system, such as the analysis system shown in FIG. 3.

DETAILED DESCRIPTION

Overview

Increasing reports of antibiotic resistant bacteria represent a global challenge to human healthcare. One strain that has emerged as an international multi-resistant high-risk clone is E. coli sequence type (ST) 131. This sequence type has been associated with fluoroquinolone resistance and the global dissemination of CTX-M antibiotic resistance genes and has recently been shown to harbour mcr-1 bearing plasmids. Previous studies have shown that treatment with fluoroquinolones or cephalosporins will select for E. coli ST131. Therefore, to improve clinical outcome, rapid and cost effective methods for the detection of this international multiresistant high-risk sequence type are crucial. Tracking the spread of this particular clonal complex has been made possible through ST identification by whole genome sequencing (WGS), pulse field gel electrophoresis (PFGE) and multi-locus sequence typing (MLST). These methods, while effective, can be expensive, labor intensive and time-consuming. One technology that can be adapted to evaluate sequence differences between DNA samples uses High Resolution Melting (HRM) analysis.

HRM is a technique used to determine whether two polymerase chain reaction (PCR) amplicons of similar size have identical sequences. This technique is similar to qPCR in that it amplifies a gene target in the presence of a fluorescent reporter dye. Following amplification, the product is exposed to an increasing temperature gradient to denature and reduce the helicity of the double-stranded oligo, releasing the fluorescent dye. Once released, the dye undergoes a conformational change that reduces the amount of fluorescence produced. A HRM-capable thermocycler will record the fluctuations in fluorescence and produce a melt curve unique to the sequence of the amplicon analyzed. This technique is capable of comparing the similarity of two amplicons because the melt curve of each oligo is determined by its nucleotide sequence, oligo length, and primary structure. The weak A-T bond is disrupted at a lower temperature than the G-C bond and therefore, A-T rich regions of the amplicon denature at lower temperatures than G-C rich regions. The distribution of these A-T or G-C rich regions of the oligo dictates the resulting melt curve and can be used to compare the similarity of amplicons from multiple samples.

HRM has previously been employed to compare the genetic similarity of pathogenic bacteria with sensitivity and specificity comparable to PFGE. These earlier methods, however, require multiple stages of preparation before PCR amplification and involve an enzymatic restriction digest. Furthermore, these methods generate a large number of oligos and increase the potential that the multiple melt profiles may overlap and obscure differences between the genomes. One alternative to these earlier methods is a targeted melting analysis of the amplicons generated during MLST. By selecting specific genes for amplification, a targeted HRM-based method both negates the need for a restriction digest and reduces the sample preparation requirements to those similar to a multiplexed qPCR. The material herein disclosed the SNP-level discriminatory power of HRM to enable rapid and cost effective differentiation of ST131 *E. coli* from non-ST131 *E. coli*.

Accordingly, methods for differentiating *E. coli* sequence type 131 are described. In one implementation, a method that employs example techniques in accordance with the present disclosure for determining *E. coli* sequence type 131 includes amplifying a gene target in the presence of a fluorescent reporter dye; exposing the gene target and the fluorescent reporter dye to an increasing temperature gradient to denature and reduce the helicity of a double-stranded oligo of the gene target; recording fluctuations in fluorescence using a High Resolution Melting analysis (HRM)-capable thermocycler; and producing a melt curve unique to the gene target.

In one implementation, a method that employs example techniques in accordance with the present disclosure for differentiating *E. coli* sequence type 131 includes recording fluctuations in fluorescence of a gene target and a fluorescent reporter dye under an increasing temperature gradient by using a High Resolution Melting analysis (HRM)-capable thermocycler; and producing a melt curve unique to the gene target.

In one implementation, a method that employs example techniques in accordance with the present disclosure for differentiating *E. coli* sequence type 131 using High Resolution Melt-curve analysis includes extracting a sample of DNA; performing a singleplex polymerase chain reaction using the sample of DNA, a buffer, and at least one multilocus sequence typing (MLST) primer resulting in at least one amplicon; performing a multiplex polymerase chain reaction using the sample of DNA and the at least one amplicon; determining a melt temperature peak using (HRM) analysis of the sample of DNA; and providing a melt profile corresponding to the sample of DNA.

One unique feature of the technology disclosed herein includes the ability to differentiate the *E. coli* sequence type 131 from other sequence types without the need to sequence PCR amplicons. Thus, this methodology is faster and cheaper than what is currently available, and a laboratory with a real time thermocycler with high resolution melt capabilities can utilize this technology without the need to have a sequencer, send it out for sequencing, or the need for whole genome sequencing.

Culturing and DNA Extraction

In a specific implementation, eleven *E. coli* strains of known sequence type (e.g., 6 ST131, 2 ST648, 1 ST404, 1 ST964, 1 ST372) can be obtained. DNA can be extracted from 10 mL overnight cultures (e.g., grown in MHB using a Qiagen DNeasy Blood & Tissue Kit™). Concentration and purity of the DNA can be evaluated, for example, with UV spectrophotometry (e.g., from BioTek Eon™) and the samples can be diluted to about 10 ng/µL.

Singleplex PCR Amplifications

Singleplex endpoint PCR reactions using ST131 DNA template and individual MLST primer sets can be performed (e.g., using a Qiagen Type-It HRM PCR kit) in a final volume of about 25 µL with about 10 ng of DNA template (or gene target) and about 12.5 pMol of each primer. In a specific example, amplification parameters can include a 5 minute denaturation at 95° C. followed by 30 cycles of a 10 second denaturation at 95° C., 30 seconds of annealing at 51° C., and 10 seconds of annealing at 72° C. The resulting amplification products can be analyzed by HRM at a 0.1° C. resolution from about 50-95° C. to determine the absolute melt curve of each amplicon. In some embodiments, derivative melt curves of MLST amplicons calculated during HRM can be compared to melt curves predicted by uMelt software to confirm sequence identity. PCR amplicons can also be separated on a 1% agarose gel and visualized with ethidium bromide to confirm that only a single product of expected size was amplified.

HRM Analysis of Multiplexed MLST Amplicons

In specific implementations, a single seven-plex reaction of all MLST primer sets can be initially tested to differentiate ST131 from non-ST131 *E. coli*. In previous experiments, this multiplex failed to have sufficient discriminatory power, and the reaction was divided into a pair of three and four-plex reactions consisting of the primer sets fumC, icd and purA (primer set 1) and adk, gyrB, mdh and recA (primer set 2). In this situation, primer concentrations may remain the same as in the singleplex reactions, and the primer combinations can be selected to minimize melt curve overlap between individual amplicons. Following amplification of these primer sets against both ST131 and non-ST131 templates with the cycling conditions described above, the MLST amplicons can be subjected to HRM analysis in the optimized range of about 80-95° C. The derivative melt curves generated can be compared between sequence types to evaluate the discriminatory power of this methodology.

Principal Component Analysis (PCA) of Multiplexed MLST Amplicons

In some implementations, the derivative melt curves of each sample may be manually compared. In other implementations, software (e.g., Qiagen ScreenClust™) can be employed to differentiate between sequence types using clustering analysis. After selecting samples by master mix, the software can automatically process the data by PCA and can cluster the samples into groups based on the variance in fluorescence between clinical isolates. A residual melt curve from the mean of normalized data can be automatically constructed for each isolate. The differential of the residual melt curves can be plotted and analyzed by PCA to construct a feature that reflects the greatest variance of each isolate from the group. The first three principal components in PCA reflect the greatest degree of variance, and these values can be graphed onto a scatterplot. The principal components can be further processed by the software (e.g., ScreenClust™) to group isolates of similar variance into clusters. With the exception of selecting the isolate samples for analysis, the software (e.g., ScreenClust™) may automate the analysis. While certain software may be only available (e.g., ScreenClust™ for the Qiagen platform), open source software can be employed to perform PCA and clustering analysis as described herein.

In a specific implementation, sequences of the MLST amplicons produced may be determined offsite (e.g., at Functional Biosciences, Inc. (Madison, Wis.) by Sanger sequencing (Big Dye V3.1, ABI3730x1)). In these specific implementations, samples can be prepared to company submission standards, and the nucleotide calling at each position can be determined by a Phred score greater than 20. The resulting sequences can then be compared to an *E. coli* MLST database (e.g., maintained at the University of Warwick (Coventry, UK)).

Development of the Methodology

Figure 1A:
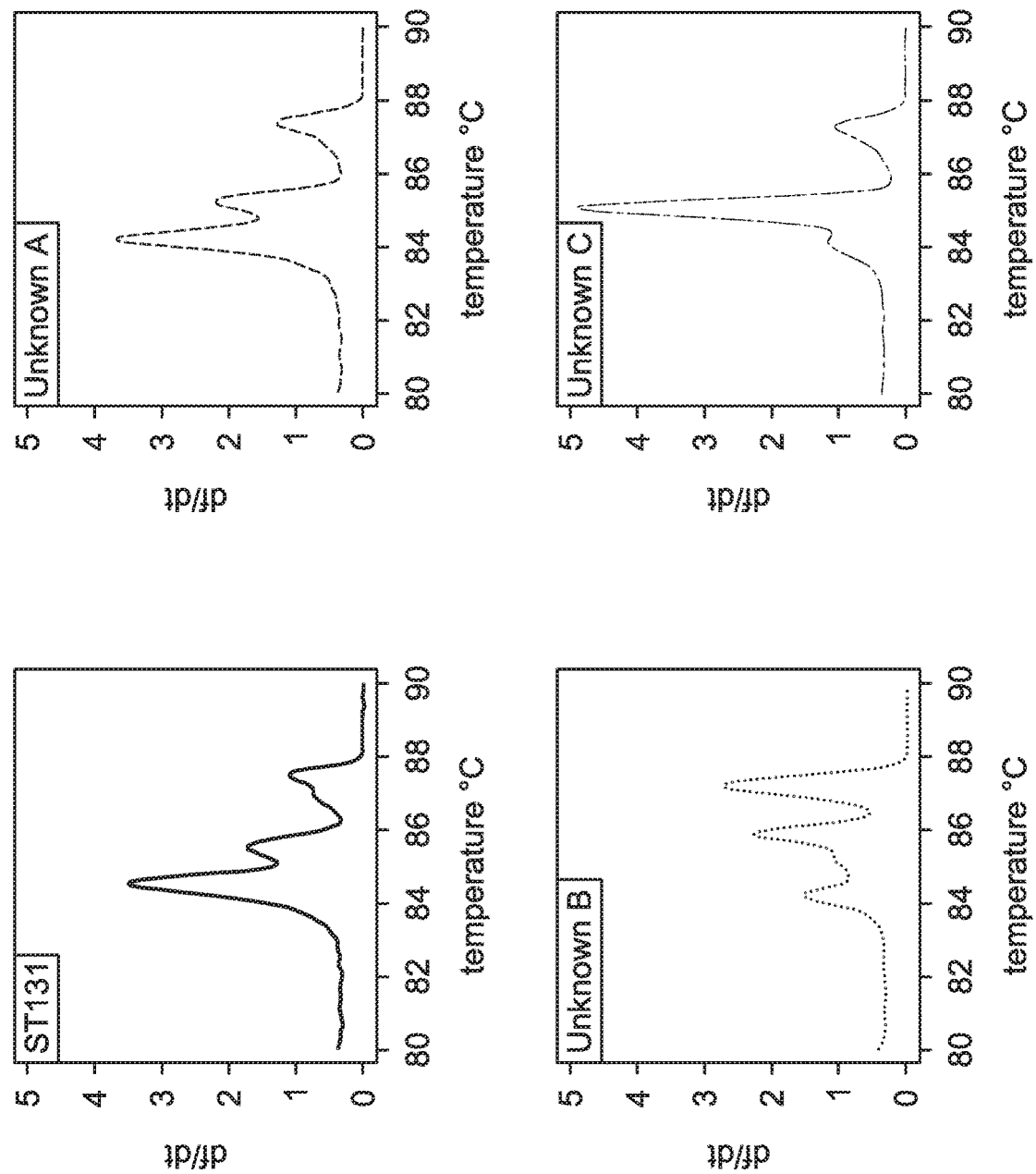
FIG. 1A is a graphical illustration depicting HRM profiles of 4 clinical isolates (1 ST131=solid line, 3 unknown sequence types=patterned line) from an adk, gyrB, mdh and recA multiplexed reaction.
Figure 1B:
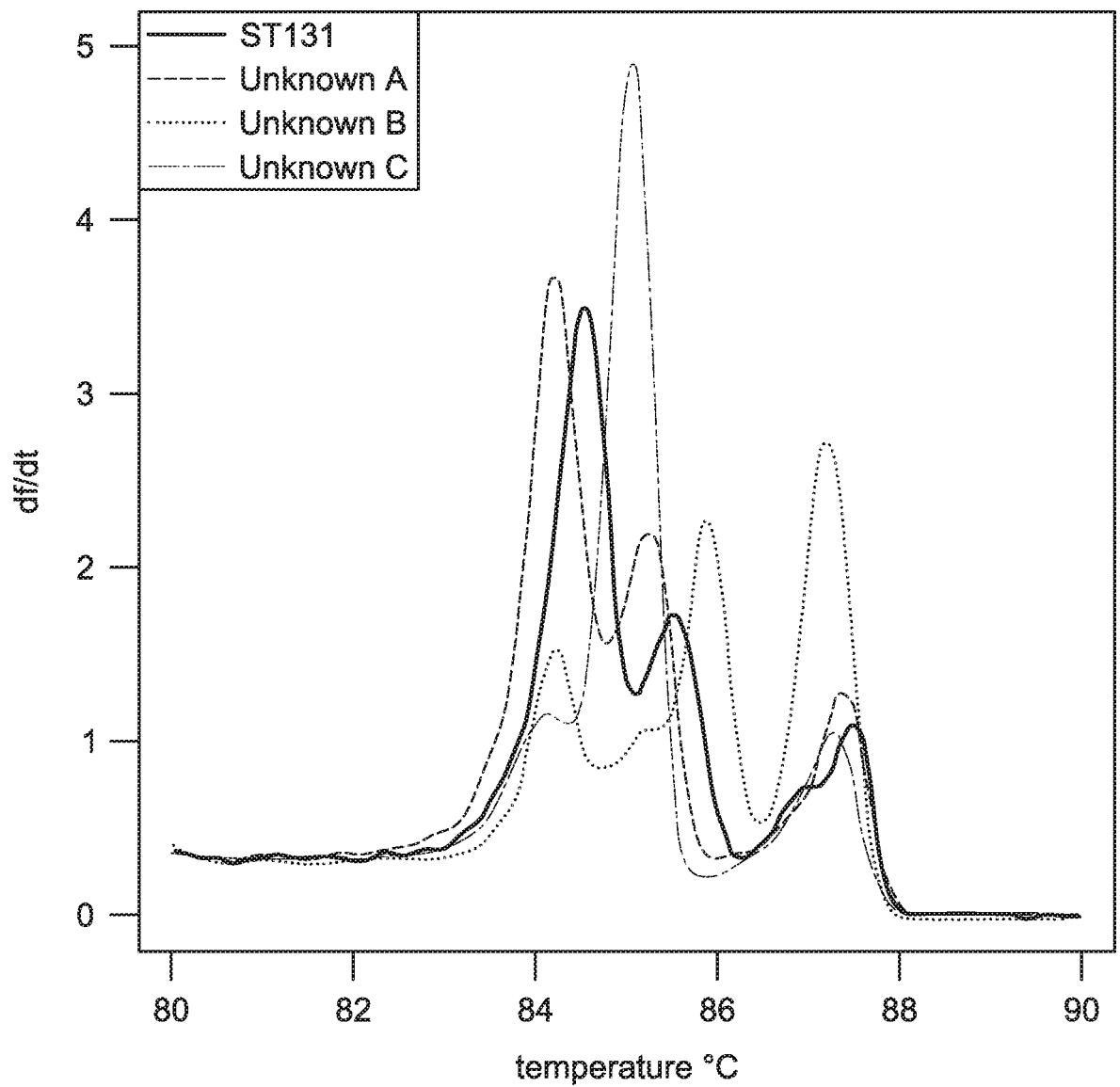
FIG. 1B is a graphical illustration depicting the four individual melt profiles from FIG. 1A presented on the same graph. By running a known ST131 sample as a control, non-ST131s can be visually identified by their lack of similarity to the ST131 melt profile.

When derivative melt curves of singleplex MLST amplicons match predicted melt curves (e.g., by uMelt software), the derivative melt curves from multiplexed HRM reactions can be compared between ST131 and non-131 *E. coli* (see FIG. 1A). In one specific instance, a direct comparison of the derivative melt curve between strains showed all ST131s shared a similar profile distinct from non-131s (see FIG. 1B).

Validation of the Methodology

In some instances, a blinded study using *E. coli* of unknown sequence types can be performed to validate the methodology. For example, three ST131 positive controls can be included with each analysis to differentiate ST131 *E. coli* from non-ST131 *E. coli*. To validate that the unknown sequence type samples identified as ST131 by HRM analysis were ST131, the sequence of their gyrB and mdh genes can be determined, for example, by Sanger sequencing. These two genes provide sufficient discrimination to identify the ST131 clonal complex.

In a specific instance, validation of the method by melt curve analysis was performed on both the Rotor-Gene Q using the HRM-Type-it kit and the ABI 7500 Fast PCR Thermocycler using the Meltdoctor HRM kit. ScreenClust™ analysis was only available for the file-type generated by the Rotor-Gene Q, and as such was performed only on data generated on that platform. The sensitivity and specificity of this methodology was compared against the sequence-typing standard of MLST amplicon sequencing.

Continuing with the specific instance above, multiplexed melt curves of ST131 *E. coli* identified 66/66 ST131 on both the Rotor-Gene Q and ABI 7500 system, displaying 100% sensitivity. One false positive on the Rotor-Gene Q and two false positives on the ABI 7500 were recorded. PCA of HRM data using ScreenClust™ software (see FIG. 2) identified 66/66 ST131 *E. coli* but also incorrectly identified three non-ST131 as ST131 from the 191 isolates evaluated. A comparison of the data (see Table 1) showed all three analyses performed with 100% sensitivity and that the derivative melt curve analysis had greater specificity than the Screenclust™ analysis.

TABLE 1

| | Cross platform sensitivity and specificity | | | | | |
|---|---|---|---|---|---|---|
| | True Positive | False Positive | True Negative | False Negative | Sensitivity % | Specificity % |
| Rotor-Gene Q | 66$^a$ (66)$^b$ | 1 (3) | 124 (122) | 0 (0) | 100 (100) | 99.2 (96.8) |
| ABI 7500 | 66$^a$ | 2 | 123 | 0 | 100 | 98.4 |

Blind validation results of the HRM methodology evaluating the panel of 191 clinical isolates consisting of 66 ST131 *E. coli* and 125 non-ST131 *E. coli*.
$^a$Values determined by comparing derivative melt curve to a ST131 standard
$^b$Values in parentheses determined by ScreenClustTM principal component analysis and clustering The ABI 7500 system does not include PCA software, but HRM data from this platform can be exported and analyzed with third-party software, for example, an open source option (e.g., the R software project). PCA is part of the functionality of the R 3.2.2 base package and the rgl and mclust packages can be used for 3D visualization and clustering, respectively. Performing the analysis with the above packages allows a user to both identify ST clusters and represent them in 2D scatterplots (see FIG. 2A) and a representative 3D interactive model (see FIG. 2B).

Antibiotic challenges from fluoroquinolones or cephalosporins used in empiric therapy selects for the survival of the ST131 *E. coli*. Rapid diagnostic tools for detecting this strain are needed to prevent the spread of this prolific strain and improve clinical outcomes for the patient. Several in-house *E. coli* sequence typing methods have recently been developed to address this, but these assays depart from established MLST scheme and require running the PCR products on an agarose gel. Conventional MLST methods provide high sensitivity and specificity but require the seven PCR products to be evaluated by gel electrophoresis to confirm amplicon generation followed by sequence analysis for each of the seven amplicons individually. Sequence type identification of bacterial proteins by matrix-assisted laser desorption/ionization time-of-flight mass spectrometry is a rapid and low cost alternative to sequence-based identification methods, but requires access to a mass spectrometer. PFGE MLST identification requires a trained technician and specialized equipment to obtain results. Sequence type identification can be obtained more quickly with Sanger sequencing but requires either an expensive on-site sequencer or paying for samples to be processed off site. This delay coupled with the processing costs makes screening for ST131 *E. coli* in a large sample size an expensive endeavor. Following DNA extraction and sample dilution, the roughly 2 hour HRM analysis outlined in this study reduces reagent costs approximately $2.00/sample compared to approximately $80.00/sample using conventional PCR amplification and sequencing to identify ST131 E. coli. As a consequence of the differences in speed and price, this gel-free HRM method facilitates screening for ST131 E. coli from large sample populations.

This methodology was initially validated on a Qiagen Rotor-Gene Q platform using the manufacturer's HRM Type-It kit. To ensure the method would work on other platforms, an additional validation was performed on an Applied Biosystems 7500 Fast System with the manufacturer recommended MeltDoctor™ HRM mix. The results of the ABI 7500 validations were similar to the Rotor-Gene Q with 100% sensitivity and 98.4% specificity vs. 100% sensitivity and 99.2% specificity (see Table 1). Both platforms report with 100% negative predictive value and all methodologies return a 98.4% or greater negative predictive value for ST131s when evaluating ESBL-producing or fluoroquinolone resistant E. coli (Table 2) using previously reported data for ST131 prevalence.

TABLE 2

Cross platform positive predictive value

| | Fluoroquinolone resistant E. coli (%) | ESBL-producing E. coli (%) | All E. coli Clinical Isolates (%) |
|---|---|---|---|
| Prevalence | 70-80 | 50-60 | 12.5-30 |
| Rotor-Gene Q | 99.7-99.8 | 99.2-99.5 | 94.7-98.2 |
| ABI-7500 Fast | 99.3-99.6 | 98.4-98.9 | 89.9-96.4 |
| Rotor-Gene Q w/ScreenClust ™ | 98.6-99.2 | 96.9-97.9 | 81.7-93.1 |

Positive predictive values for this methodology calculated using prevalence of ST131 E. coli in antibiotic resistant subpopulations of clinical isolates.

PCA is a data reduction tool that can condense complex data sets into simple visual representations. In one specific study, visual analysis made it possible to evaluate melt profiles of 36 samples at once without requiring individual comparisons to a ST131 melt curve standard. PCA of these samples maintained the same sensitivity as the derivative melt curve, but a lower specificity. The scatterplots produced by PCA reflect variance between the samples and as such, analyzing a large number of closely related sequence types may prevent distinct clusters from being produced. In this case, PCA can be used to quickly rule out samples that are not ST131s followed by derivative melt curve analysis of the remaining samples.

In a specific implementation, the mass of DNA in the reaction affected the shape of the derivative melt curve. Altering the amount of DNA used in the PCR amplification step beyond a 2-fold concentration affects both the observed melting temperature and the magnitude of the melt peaks. The technical error of using too much DNA can be identified by the derivative melt curve analysis because the resulting curve is similar to the ST131 standards. However, this profile similarity is not corrected in PCA and a sample with a different DNA concentration can be placed askew on the principal component cluster-plot.

The real-time multiplex PCR reaction followed by HRM analysis disclosed herein is a one-step PCR reaction that can identify ST131 E. coli from other sequence types in roughly 2 hours (e.g., less than 95 minutes for amplification+15 minutes for data analysis). If direct sequencing of amplicons is required to determine the specific subsets of ST131 E. coli, an initial screen can differentiate the non-ST131 and reduce the number of organisms that need to be further evaluated. Further, data analysis software from either commercial vendors or open source providers is available to streamline the analysis on Windows, Mac or Linux operating systems. This HRM methodology can be performed on multiple platforms with a high degree of sensitivity and specificity and is both faster and less expensive than conventional sequence typing methods.

Example 1

In the following specific implementation, three isolates were be used to optimize multiplex HRM analysis. DNA can be extracted using the Qiagen™ DNeasy Blood and Tissue Mini-Prep kit. It is contemplated that DNA and/or a gene target can be extracted and/or obtained using a variety of methods, which may be automated. Singleplex PCR was performed using 10 ng of DNA, Type-iT HRM buffer and MLST primers (adk, fumC, gyrB, icd, mdh, purA and recA) followed by multiplex PCR. In this specific implementation, amplicon sizes ranged from about 452 to 932 base points (bp). It is contemplated that amplicon sizes can include other ranges and/or sizes (e.g., approximately 450 to approximately 1035 base pair (bp)). Melt temperature (Tm) peaks were determined by performing HRM analysis at 0.1° C. resolution from about 50-95° C. on a Rotor-Gene Q 5-Plex HRM system. Melt profiles were analyzed using Screenclust™ software with principal component analysis (e.g., a statistical procedure that uses an orthogonal transformation to convert a set of observations of possibly correlated variables into a set of values of linearly uncorrelated variables called principal components). In one specific instance in validating the optimized assay, a blinded study using 191 E. coli of ST131 and unknown sequence types was evaluated.

In the specific implementation above, primers used in the assay amplified singled products with Tm peaks of 86.30 (adk), 86.94 (fumC), 86.86 (gyrB), 84.78 (icd), 84.97 (mdh), 87.37 (purA) and 87.58° C. (recA). After establishing the singleplex assays, primers were multiplexed as follows: set 1: adk, gyrB, mdh, recA and set 2: fumC, icd, and purA—without affecting established melt curves. Following an initial activation step of 5 minutes at 95° C., the multiplexed reactions were amplified using the following conditions: 10 seconds at 95° C., 30 seconds at 51° C. and 10 seconds at 72° C. for 30 cycles before proceeding to amplicon melting. HRM analysis of the multiplex was performed with the optimized range of 80-95° C. Validation of the assay using blinded E. coli samples established that this methodology had a specificity of about 99% (true negatives (TN)=124, false positive (FP)=1) and sensitivity of 100% (true positives (TP)=66, false negatives (FN)=0). This sequence type identification methodology was repeated on an ABI 7500 Fast Real-Time PCR system using the following conditions. After an initial 10 minute denaturation at 95° C., PCR amplicons were generated by cycling for 15 seconds at 95° C., 30 seconds at 51° C. and 20 seconds at 72° C. for a total of 30 cycles. After this the products were exposed to a temperature gradient from 80-95° C. during HRM analysis.

The MLST multiplexed HRM analysis developed in this study differentiates ST131 from non-ST131 E. coli without the need for sequence analysis. This methodology can identify ST131 E. coli in roughly 2 hours. Therefore this assay is a fast and inexpensive alternative to sequence-based identification of ST131 E. coli and can be performed in any lab with a HRM-capable instrument and principle component analysis software.

As shown in FIG. 3, an analysis system 100 can include a controller 102 configured to control and operate the methods for determining *E. coli* sequence type 131 described herein. In implementations, the analysis system 100 can include components, instruments, and/or devices for determining *E. coli* sequence type 131, such as a spectrophotometer, sequencing instrumentation, a PCR system, a sampling system, a thermocycler and/or an HRM system. In embodiments, the controller 102 can be disposed in the analysis system 100 and/or can be disposed separately from the analysis system 100.

Illustrated in FIG. 3, an analysis system 100, including some or all of its components, can operate under computer control. For example, a processor 104 can be included with or in an analysis system 100 and/or controller 102 to control the components and functions of analysis system 100 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the analysis system 100. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

The analysis system 100 can be coupled with a controller 102 for controlling the analysis system 100. The controller 102 can include a processor 104, a memory 106, and a communications interface 108. The processor 104 provides processing functionality for the analysis system 100/controller 102 and can include any number of processors, micro-controllers, or other processing systems, and resident or external memory for storing data and other information accessed or generated by the analysis system 100/controller 102. The processor 104 can execute one or more software programs that implement techniques described herein. The processor 104 is not limited by the materials from which it is formed or the processing mechanisms employed therein and, as such, can be implemented via semiconductor(s) and/or transistors (e.g., using electronic integrated circuit (IC) components), and so forth.

The controller 102 may include a memory 106. The memory 106 can be an example of tangible, computer-readable storage medium that provides storage functionality to store various data associated with operation of the analysis system 100/controller 102, such as software programs and/or code segments, or other data to instruct the processor 104, and possibly other components of the analysis system 100/controller 102, to perform the functionality described herein. Thus, the memory 106 can store data, such as a program of instructions for operating the analysis system 100 (including its components), and so forth. It should be noted that while a single memory 106 is described, a wide variety of types and combinations of memory (e.g., tangible, non-transitory memory) can be employed. The memory 106 can be integral with the processor 104, can comprise stand-alone memory, or can be a combination of both.

The memory 106 can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the analysis system 100 and/or the memory 106 can include removable integrated circuit card (ICC) memory, such as memory provided by a subscriber identity module (SIM) card, a universal subscriber identity module (USIM) card, a universal integrated circuit card (UICC), and so on.

The controller 102 may include a communications interface 108. The communications interface 108 can be operatively configured to communicate with components of the analysis system 100. For example, the communications interface 108 can be configured to transmit data for storage in the analysis system 100, retrieve data from storage in the analysis system 100, and so forth. The communications interface 108 can also be communicatively coupled with the processor 104 to facilitate data transfer between components of the analysis system 100 and the processor 104 (e.g., for communicating inputs to the processor 104 received from a device communicatively coupled with the analysis system 100/controller 102). It should be noted that while the communications interface 108 is described as a component of an analysis system 100/controller 102, one or more components of the communications interface 108 can be implemented as external components communicatively coupled to the analysis system 100 via a wired and/or wireless connection. The analysis system 100 can also comprise and/or connect to one or more input/output (I/O) devices (e.g., via the communications interface 108), including, but not necessarily limited to: a display, a mouse, a touchpad, a keyboard, and so on.

The communications interface 108 and/or the processor 104 can be configured to communicate with a variety of different networks, including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface 108 can be configured to communicate with a single network or multiple networks across different access points.

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system, or circuit. Further, elements of the blocks, systems, or circuits may be implemented across multiple integrated circuits. Such integrated circuits may comprise various integrated circuits, including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block, or circuit may be implemented using its software or firmware equivalent. In other instances, one part of a given system, block, or circuit may be implemented in software or firmware, while other parts are implemented in hardware.

The following discussion describes example techniques for operating an analysis system 100 for determining E. coli sequence type 131, such as the analysis system 100 shown in FIG. 3. FIGS. 4 through 6 depict example processes 400, 500, and 600 for operating the analysis system 100 shown in FIG. 3.

As shown in FIG. 4, a gene target is amplified in the presence of a fluorescent reporter dye (Block 402). Then, the gene target and the fluorescent reporter dye is exposed to an increasing temperature gradient to denature and reduce the helicity of a double-stranded oligo of the gene target (Block 404). Next, fluctuations in fluorescence are recorded using a High Resolution Melting analysis (HRM)-capable thermocycler (Block 406). Then, a melt curve unique to the gene target is produced (Block 408).

As shown in FIG. 5, fluctuations in fluorescence of a gene target and a fluorescent reporter dye are recorded under an increasing temperature gradient by using a High Resolution Melting analysis (HRM)-capable thermocycler (Block 502). Then, a melt curve unique to the gene target is produced (Block 504).

As shown in FIG. 6, a sample of DNA is extracted (Block 602). Then, a singleplex polymerase chain reaction is performed using the sample of DNA, a buffer, and at least one multilocus sequence typing (MLST) primer resulting in at least one amplicon (Block 604). Next, a multiplex polymerase chain reaction using the sample of DNA and the at least one amplicon is performed (Block 606). Subsequently, a melt temperature peak is determined using (HRM) analysis of the sample of DNA (Block 608). Then, a melt profile corresponding to the sample of DNA is provided (Block 610).

It is to be understood that embodiments of the present invention described above are intended to be merely exemplary. Those skilled in the art will recognize, or be able to ascertain using no more than routine experimentation, numerous equivalents to the specific procedures described herein. All such equivalents are considered to be within the scope of the present invention and are covered by the following claims.

It is further contemplated that any embodiment or implementation of the disclosure manifested above as a system or method may include at least a portion of any other embodiment or implementation described herein. Those having skill in the art will appreciate that there are various embodiments or implementations by which systems and methods described herein can be implemented, and that the implementation will vary with the context in which an embodiment of the disclosure is deployed.

Furthermore, it is to be understood that although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A method for determining E. coli sequence type 131, comprising:
   amplifying a gene target in the presence of a fluorescent reporter dye via a first multiplex reaction of a first portion of the gene target with a first primer set including primers for each of fumC, icd and purA and a second multiplex of a second portion of the gene target with a second primer set including primers for each of adk, gyrB, mdh and recA;
   exposing the gene target and the fluorescent reporter dye to an increasing temperature gradient to denature and reduce the helicity of a double-stranded oligo of the gene target;
   recording fluctuations in fluorescence using a High Resolution Melting analysis (HRM)-capable thermocycler; and
   producing a melt curve unique to the gene target.

2. The method for determining E. coli sequence type 131 of claim 1, wherein amplifying a gene target includes using approximately 10 nanograms (ng) of DNA.

3. The method for determining E. coli sequence type 131 of claim 1, wherein amplifying a gene target includes heating the gene target for approximately 10 seconds at approximately 95° C., 30 seconds at approximately 51° C., and 10 seconds at approximately 72° C.

4. The method for determining E. coli sequence type 131 of claim 1, wherein exposing the gene target and the fluorescent reporter dye to an increasing temperature gradient includes exposing the gene target to a temperature gradient from approximately 80-95° C.

5. The method for determining E. coli sequence type 131 of claim 1, wherein performing the amplifying step until the producing a melt curve takes less than 95 minutes.

6. A method for differentiating E. coli sequence type 131, comprising:
   amplifying a gene target in the presence of a fluorescent reporter dye via a first multiplex reaction of a first portion of the gene target with a first primer set including primers for each of fumC, icd and purA and a second multiplex reaction of a second portion of the gene target with a second primer set including primers for each of adk, gyrB, mdh and recA;
   recording fluctuations in fluorescence of the gene target and the fluorescent reporter dye under an increasing temperature gradient by using a High Resolution Melting analysis (HRM)-capable thermocycler;
   producing a melt curve unique to the gene target; and
   comparing a melt curve obtained from recording the fluctuations in fluorescence of a gene target with at least one previously obtained melt curve.

7. The method for differentiating E. coli sequence type 131 of claim 6, wherein the gene target includes approximately 10 nanograms (ng) of DNA.

8. The method for differentiating E. coli sequence type 131 of claim 6, wherein the increasing temperature gradient includes exposing the gene target to a temperature gradient from approximately 80-95° C.

* * * * *